United States Patent [19]

Gasson

[11] 4,314,941
[45] Feb. 9, 1982

[54] AMINOCARBONYLMETHYL ETHERS OF CLAVULANIC ACID, A PROCESS FOR THEIR PREPARATION AND USE

[75] Inventor: Brian C. Gasson, Redhill, England

[73] Assignee: Beecham Group Limited, England

[21] Appl. No.: 973,749

[22] Filed: Dec. 26, 1978

[30] Foreign Application Priority Data

Jan. 26, 1978 [GB] United Kingdom ............... 03129/78

[51] Int. Cl.³ .................. C07D 498/04; A61K 31/42
[52] U.S. Cl. ................................. 260/245.3; 424/272
[58] Field of Search ..................... 260/307 F, 307 FA; 424/272

[56] References Cited

FOREIGN PATENT DOCUMENTS 2646004  4/1977  Fed. Rep. of Germany ... 260/307 R

OTHER PUBLICATIONS

Hackh's Chemical Dictionary, p. 80.
"Nomenclature of Organic Chemistry", 1979 edition, I.U.P.A.C., pp. 202, 206.
"Naming Organic Compounds", 2nd edition, Banks, p. 191.
"An Introduction to Chemical Nomenclature", 4th edition, Cahn, p. 98.
"Condensed Chemical Dictionary", 9th edition, p. 16.
"Organic Chemistry", vol. 1, (Finar), p. 222.
"Organic Chemistry, 2nd Edition, 1964", (Cram et al.), pp. 90-91.
"King Zett's Chemical Encyclopaedia", 9th edition, p. 18.

Primary Examiner—Mark L. Berch
Attorney, Agent, or Firm—Jacobs & Jacobs

[57] ABSTRACT

The compound of the formula (I):

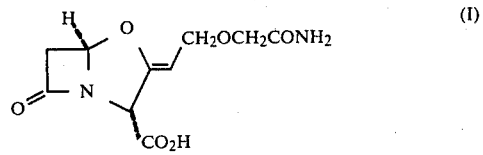

and pharmaceutically acceptable salts and esters thereof, are useful for their β-lactamase inhibitory activity and synergized penicillins and cephalosporins in the treatment of bacterial infections.

13 Claims, No Drawings

AMINOCARBONYLMETHYL ETHERS OF CLAVULANIC ACID, A PROCESS FOR THEIR PREPARATION AND USE

Belgian Patent No. 847045 discloses inter alia that ethers of clavulanic acid are useful β-lactamase inhibitors which enhance the effectiveness of penicillins and cephalosporins. It has now been discovered that a previously unprepared ether of clavulanic acid possesses favourable β-lactamase inhibitory properties and so is favoured as a synergist.

The present invention provides the compound of the formula (I):

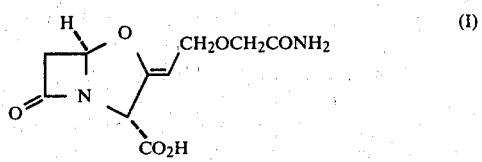

and salts and esters thereof.

Suitably the compound of this invention is in the form of the free acid of the formula (I).

Suitably the compound of this invention is in the form of a salt of the compound of the formula (I).

Apt salts of the compound of the formula (I) include alkali metal salts, alkaline earth metal salts and salts with nitrogenous bases. Thus suitable salts include the lithium, sodium, potassium, calcium, magnesium, ammonium and alkylamine salts such as salts with primary alkyl amines, secondary alkylamines, tertiary alkylamines and the like (such as the 2-amino-2-methylpropane, diethylamine, triethylamine, pyrrolidine and the like salts).

Most suitably the salt of the compound of the formula (I) is pharmaceutically acceptable. Non-pharmaceutically acceptable salts may be used as intermediates, for example in the preparation of pharmaceutically acceptable salts or of esters.

Suitable esters of the compound of the formula (I) include those of the formulae (II) and (III):

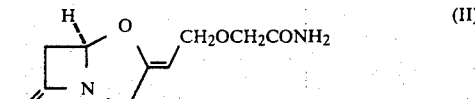

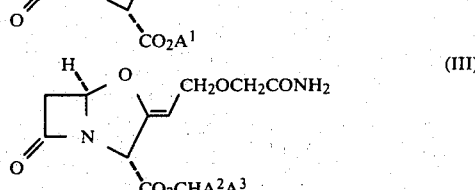

wherein $A^1$ is an alkyl group of up to 4 carbon atoms, an alkenyl group of up to 4 carbon atoms, an alkynyl group of up to 4 carbon atoms or an alkyl group of up to 4 carbon atoms substituted by a halogen atom or a hydroxyl group or an alkoxyl or acyloxyl group of up to 4 carbon atoms or by an acetyl or benzoyl group; $A^2$ is a hydrogen atom or phenyl, chlorophenyl, methoxyphenyl, bromophenyl or nitrophenyl group; and $A^3$ is a phenyl, chlorophenyl, methoxyphenyl, bromophenyl or nitrophenyl group.

Esters of the compound of the formula (I) may be used as to enhance the effectiveness of penicillins or cephalosporins. Many esters of the compound of the formula (I) are useful intermediates in the preparation of the compound of the formula (I) or its salts.

Suitable synergists include those of the formulae (II) and (III) above. Certain particularly apt synergists in vivo include those of the formula (IV):

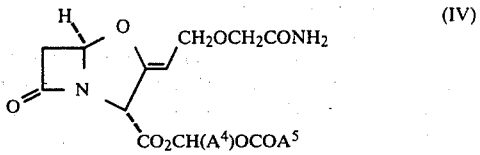

wherein $A^4$ is a hydrogen atom or a methyl group when $A^5$ is an alkyl or alkoxyl group of up to 4 carbon atoms or a phenyl or benzyl group or $A^4$ is attached to $A^5$ to form a phenyl ring. Thus suitable esters of the compound of the formula (IV) include the acetoxymethyl, α-acetoxyethyl, pivaloyloxymethyl, α-pivaloyloxyethyl, ethoxycarbonyloxymethyl, α-ethyoxycarbonyloxyethyl, phthalidyl and like esters.

The esters of the formula (II) can serve as intermediates in the preparation of salts of the compound of the formula (I) by hydrolysis.

The esters of the formula (III) can serve as intermediates in the preparation of the compound of the formula (I) or its salts via hydrogenation.

As has been previously stated, the compound of the formula (I) its salts and esters thereof have valuable therapeutic properties. Accordingly in a further aspect, this invention provides a pharmaceutical composition which comprises the compound of the formula (I) or a pharmaceutically acceptable salt or ester thereof together with a pharmaceutically acceptable carrier.

The compositions of the invention include those in a form adapted for oral, topical or parenteral use and may be used for the treatment of infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colourings, flavours preservatives, and disintegrants in accordance with conventional pharmaceutical practice in the manner well understood by those skilled in the art of formulating antibiotics. The compositions of this invention may be formed by bringing together the components in known manner (for example as in actual use or as described in the literature).

Injectable or infusable compositions of the compound of the formula (I) or its salts are particularly suitable as high tissue levels of the synergist can occur after administration by injection or infusion. Thus, one preferred composition aspect of this invention comprises the compound of the formula (I) or its pharmaceutically acceptable salt in sterile form, for example a conventional injectable alkali metal salt such as the sterile sodium or potassium salt. In accordance with conventional practice such injectable compositions will be made up in a sterile pyrogen-free liquid such as water for injection B.P.

Unit dose compositions comprising the compound of the formula (I) or a salt thereof adapted for oral administration form a further preferred composition aspect of this invention.

Under certain conditions, the effectiveness of oral compositions of the compound of the formula (I) and its salts can be improved if such compositions contain a buffering agent or an enteric coating agent such that the compounds of the invention do not have prolonged contact with highly acidic gastric juice. Such buffered or enterically coated compositions may be prepared in accordance with conventional pharmaceutial practice.

The compound of the formula (I) or its pharmaceutically acceptable salt may be present in the composition as sole therapeutic agent or it may be present together with a further therapeutic agent such as a penicillin or cephalosporin. Suitable penicillins and cephalosporins for inclusion in such synergistic compositions include not only those known to be highly susceptible to β-lactamases but also those which have a good degree of intrinsic resistance to some β-lactamases.

Naturally if the penicillin or cephalosporin present in the synergistic composition is not suitable for oral administration then the composition will be adapted for parenteral administration.

Penicillins suitable for inclusion in orally administrable compositions of this invention include benzylpenicillin, phenoxymethylpenicillin, propicillin, amoxycillin, ampicillin, epicillin, cyclacillin and other orally active penicillins and their pharmaceutically acceptable salts and in-vivo hydrolysable esters and aldehyde and ketone adducts of those penicillins containing a 6-α-aminoacylamido side chain and their pharmaceutically acceptable salts. Suitable penicillin in-vivo hydrolysable esters include the acetoxymethyl, pivaloyloxymethyl, α-ethoxycarbonylethyl and phthalidyl esters of ampicillin or amoxycillin or the phenyl, tolyl and indanyl α-esters of carbenicillin and ticarcillin and pharmaceutically acceptable salts thereof. Suitable aldehyde and ketone adducts of penicillins containing a 6-α-aminoacylamido side chain include the formaldehyde and acetone adducts of ampicillin or amoxycillin such as metampicillin and hetacillin and their salts. Suitable penicillins for inclusion in injectably or infusably administrable compositions include the pharmaceutically acceptable salts of benzylpenicillin, phenoxymethylpenicillin, carbenicillin, propicillin, ampicillin, amoxycillin, epicillin ticarcillin and cyclacillin, azlocillin and the like.

Cephalosporins suitable for inclusion in orally administrable compositions of this invention include cephalexin, cephradine, cephalogylcine and their pharmaceutically acceptable salts and other known cephalosporins and their pharmaceutically acceptable salts and in-vivo hydrolysable esters and aldehyde and ketone adducts of those cephalosporins containing a 7-α-aminoacylamido side chain and their pharmaceutically acceptable salts. Suitable cephalosporins for inclusion in the injectable or infusable compositions of this invention include the pharmaceutically acceptable salts of cephaloridine, cephalothin, cefazolin, cephalexin, cephacetrile, cephamandole, cephapirin, cephradine, cephaloglycine and other known cephalosporins.

When present in a pharmaceutical composition together with a penicillin or cephalosporin, the weight ratio of the compound of the formula (I) or its salt or ester present to penicillin or cephalosporin present may be from, for example, 10:1 to 1:10, for example 3:1 to 1:3 and usually 1:1 to 1:2.

Compositions of this invention may be used for the treatment of infections of inter alia, the respiratory tract, the urinary tract and soft tissues in humans.

Compositions of this invention may also be used to treat infections of domestic animals such as mastitis in cattle.

The penicillin or cephalosporin in a synergistic composition of this invention will normally be present at approximately the amount conventionally used when that penicillin or cephalosporin is the sole therapeutic agent used in the treatment of infection.

Suitably the weight of the compound of the formula (I) or its salt or ester in a unit dosage form of this invention will be from 50 to 500 mg and more suitably from 50 to 250 mg.

In general the total quantity of antibacterial agents present in a synergistic composition of this invention will not be greater than 1500 mg and will usually be between 100 and 1000 mg.

Normally between 500 and 3000 mg of the synergistic compositions of the invention will be administered each day of treatment (to an average 70 kg adult). However, for the treatment of severe systemic infections or infections of particularly intransigent organisms, higher doses may be used in accordance with clinical practice.

Particularly favoured compositions of this invention will contain from 150 to 1000 mg of amoxycillin, ampicillin or an in-vivo hydrolysable ester or aldehyde or ketone adduct thereof or a pharmaceutically acceptable salt thereof and from 50 to B 500 mg of the compound of the formula (I) or a pharmaceutically acceptable salt thereof; and a pharmaceutically acceptable carrier therefor.

More suitably the compositions will contain from 200 to 500 mg of amoxycillin or a salt thereof or ampicillin or a salt thereof. More suitably the compositions will contain from 50 to 150 mg of the compound of the formula (I) or a salt thereof.

Most suitably the compositions will contain a salt of the compound of the formula (I).

The materials present in such compositions may be hydrated. Thus the ampicillin may be present as ampicillin trihydrate and the amoxycillin may be present as amoxycillin trihydrate.

The preferred penicillin for use in such compositions is amoxycillin, for example as amoxycillin trihydrate in orally administrable compositions or as sodium amoxycillin in injectable compositions.

The weights of the antibiotics in such compositions are expressed on the basis of pure free antibiotic equivalent present and not on the basis of salt, ester, adduct or hydrate.

The present invention also provides a process for the preparation of the compound of the formula (I) and its salts and esters which process comprises the reaction of an ester of clavulanic acid with diazoacetamide and thereafter if desired converting the thus formed ester of the compound of the formula (I) to the compound of the formula (I) or its salt and thereafter if desired converting the thus formed acid or salt into an alternative salt or other ester.

The reaction of the clavulanate ester with diazoacetamide will generally take place in an inert organic solvent such as haloalkane, for example dichloromethane, chloroform or the like or an ester solvent such as ethyl acetate or the like.

Normally a Lewis acid catalyst such as boron trifluoride etherate is employed.

In general the reagents are mixed at a depressed temperature such as −80° to −50°. The reaction mixture is then usually allowed to warm slowly, for example to −30° to −20° C. and then eventually to about 0°.

The desired ester can be obtained from the reaction mixture by washing with sodium bicarbonate solution and with water and thereafter drying the organic phase and removing the solvent, for example by evaporation. The desired ester may then be obtained by chromatography for example over kieselgel, silica or the like using a fairly polar solvent such as ethyl acetate (tlc with permanganate spray may be used to identify the correct fractions. Evaporation of the solvent from the collected fractions yields the purified ester.

If it is desired to produce the compound of the formula (I) or its salt then a hydrogenolysable or hydrolysable ester is employed. Thus, for example, an ester of the formula (II) such as the methoxymethyl ester may be hydrolysed under mildly basic conditions, for example pH 8.5–9.5, to yield a salt of the compound of the formula. Alternatively, a compound of the formula (III) may be employed and hydrogenolysed to yield the compound of formula (I) or, if a base is present, a salt thereof.

Belgian Patent Specification No. 8474045 may be inspected for suitable reaction conditions.

The processes of this invention may be adapted to prepare such compounds as:
9-O-Carboxamidomethylclavulanic acid
Lithium 9-O-Carboxamidomethylclavulanate
Sodium 9-O-carboxamidomethylclavulanate
Potassium 9-O-carboxamidomethylclavulanate
Benzyl 9-O-carboxamidomethylclavulanate
p-Bromobenzyl 9-O-carboxamidomethylclavulanate
p-Methoxybenzyl 9-O-carboxamidomethylclavulanate
p-Nitrobenzyl 9-O-carboxamidomethylclavulanate
Methyl 9-O-carboxamidomethylclavulanate
Methoxymethyl 9-O-carboxamidomethylclavulanate

EXAMPLE 1

Benzyl 9-O-carboxamidomethylclavulanate

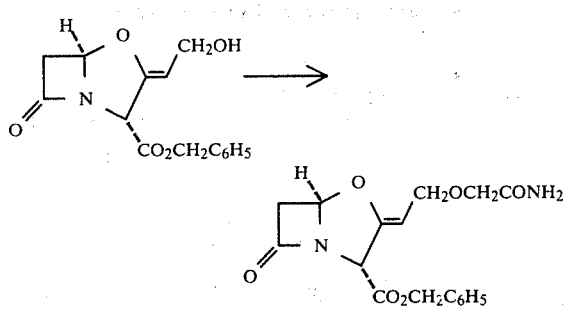

A stirred solution of benzyl clavulanate (1.156 mg) in methylene chloride (10 mls) was cooled in a dry-ice-acetone bath and treated with boron trifluoride etherate (0.3 mls). A slurry of diazoacetamide (334 mgs) in methylene chloride (15 mls) was then added and the mixture allowed to warm to −30°. The temperature was held at −25° to −30° for ½ hour, and then allowed to warm to 0°. Excess sodium bicarbonate solution was then added and the organic phase separated. The aqueous phase was extracted twice with chloroform, and the combined organic phases were washed with brine, dried over magnesium sulphate and evaporated. The product was isolated by column chromatography (Kieselgel, ethyl acetate as eluent), to give 212 mgs of white solid. Recrystallisation from ethyl acetate/cyclohexane gave the product as 160 mgs of white solid, m.pt 121°–123°. Analysis: found; C, 58.75; H, 5.21; N, 7.82: $C_{17}H_{18}N_2O_6$ requires: C, 58.95; H, 5.24; N, 8.09. I.R. $\nu_{max}$ (nujol) 3350, 3170, 1795, 1735, 1693 and 1620 cm$^{-1}$. N.M.R. $\delta$(CDCl$_3$) 2.99 (1H, d, J=17 Hz). 3.44 (1H, dd, J=3 and 17 Hz). 3.80 (2H, s), 4.05 (2H, d, J=8 Hz), 4.73 (1H, broad t, J=8 Hz), 5.03 (1H, s), 5.13 (2H, s), 5.63 (1H, d, J=3 Hz), 6.00 (1H, broad singlet), 6.35 (1H, broad singlet), 7.27 (5H, s).

EXAMPLE 2

Sodium 9-O-carboxamidomethylclavulanate

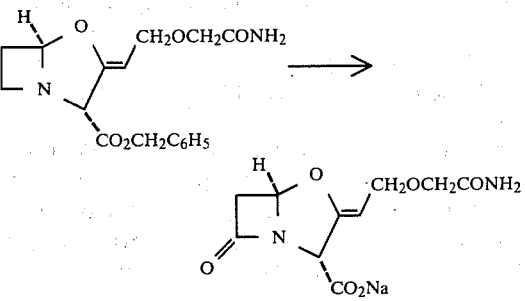

A solution of benzyl 9-O-carboxamidomethyl clavulanate (155 mgs) in tetrahydrofuran (10 ml) was hydrogenated over 10% palladium charcoal (50 mgs) for 35 mins. The solution was filtered through celite and the filter cake washed with tetrahydrofuran. The combined filtrates were diluted with water and treated with a solution of sodium bicarbonate (37.8 mgs) in water. Most of the tetrahydrofuran was removed under vacuum, and the aqueous solution was extracted three times with ethyl acetate. The solution was filtered through celite, evaporated and the residue dried over phosphorus pentoxide to yield sodium 9-O-carboxamidomethylclavulanate (82 mgs).

I.R. $\nu$max (KBr) 1778, 1670 and 1610 cm$^{-1}$,
N.M.R. $\delta$ (D$_2$O) 2.95 (1H, d, J=17 Hz), 3.43 (1H, dd, J=3 and 17 Hz) 3.85 (2H, s). 4.15 (2H, d, J=8 Hz), 4.79 (1H, broad t, J=8 Hz), 4.84 (1H, broad s), 5.60 (1H, d, J=3 Hz).

EXAMPLE 3 p-Nitrobenzyl 9-O-carboxamidomethylclavulanate

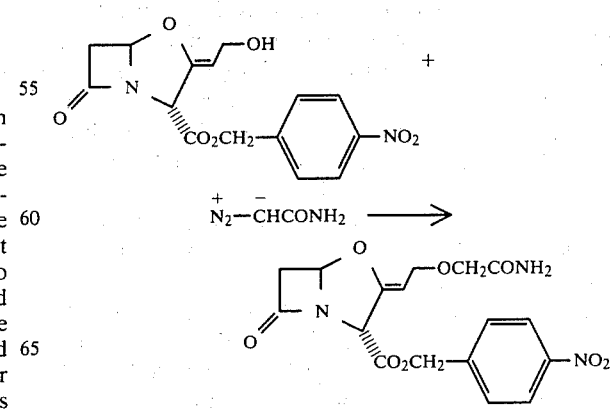

A stirred mixture of p-nitrobenzyl clavulanate (1.0 gm) and diazoacetamide (255 mg) in dry methylene chloride (15 ml) was cooled in a dry ice-acetone bath, and treated with boron trifluoride etherate (0.2 ml). The mixture was allowed to warm to −30° and then maintained at −30° to −20° for ½ hr. The mixture was then allowed to warm to 0° and treated with excess sodium bicarbonate solution. The organic phase was separated and the aqueous phase extracted twice with chloroform. The combined organic phases were washed with brine, dried over magnesium sulphate and evaporated. The product was obtained by column chromatography of the residue using gradient elution (Kieselgel 1:1 ethyl acetate:cyclohexane going to neat ethyl acetate as eluent).

Yield 332 mg. m.pt. 148–150 from ethyl acetate.

I.R. $v_{max}$ (Nujol) 3320, 3150, 1810, 1745, 1693 and 1648 cm$^{-1}$.

N.M.R. δ (D$_6$ DMSO) 3.12 (1H, d, J=17 Hz), 3.66 (1H, dd, J=3 and 17 Hz), 3.73 (2H, s), 4.07 (2H, d, J=7 Hz), 4.86 (1H, broad t, J=7 Hz), 5.36 (2H, s), 5.44 (1H, broad s), 5.76 (1H, d, J=3 Hz), 7.15 (2H, broad), 7.66 (2H, d, J=9 Hz), 8.24 (2H, d, J=9 Hz).

EXAMPLE 4

Methoxymethyl 9-O-carboxamidomethylclavulanate

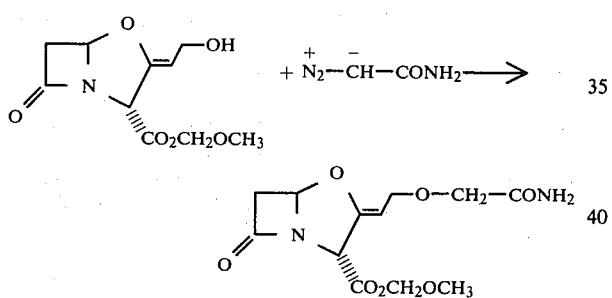

A stirred mixture of diazoacetamide (255 mg), and methoxymethyl clavulanate (729 mg) in dry methylene chloride (15 ml) was cooled in a dry-ice acetone bath, and treated with boron trifluoride etherate (0.2 ml). The mixture was allowed to warm to −30° and maintained at −30° to −20° for ½ hr. The mixture was then allowed to warm to 0° and treated with excess sodium bicarbonate solution. The organic phase was separated and the aqueous phase extracted twice with chloroform. The combined organic phases were washed with brine, dried over magnesium sulphate and evaporated. The product was obtained by column chromatography of the residue (Kieselgel, ethyl acetate as eluent).

Yield 239 mg of pale yellow gum.

I.R. $v_{max}$ (film) 3420, 3320, 1805, 1755, and 1690 cm$^{-1}$.

N.M.R. δ (CDCl$_3$) 3.06 (1H, d, J=17 Hz), 3.47 (3H, s), 3.51 (1H, dd, J=3 and 17 Hz), 3.90 (2H, s), 4.15 (2H, d, J=7 Hz), 4.89 (1H, broad t, J=7 Hz), 5.10 (1H, broad s), 5.26 (1H, d, J=6 Hz), 5.36 (1H, d, J=6 Hz), 5.72 (1H, d, J=3 Hz), 5.9–6.7 (2H, broad).

EXAMPLE 5

Methyl 9-O-carboxamidomethylclavulanate

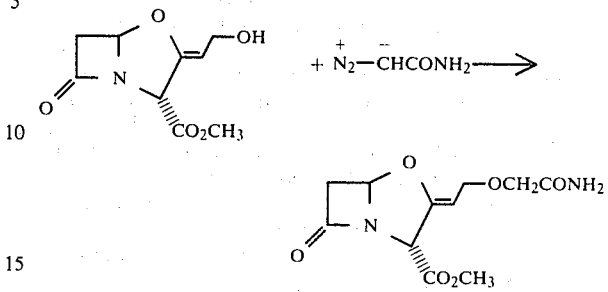

A stirred mixture of diazoacetamide (255 mg) and methyl clavulanate (639 mg) in dry methylene chloride (15 ml), was cooled in a dry-ice-acetone bath and treated with boron trifluoride etherate (0.2 ml). The mixture was then allowed to warm to −30° and maintained at −30° to −20° for ½ hr. The mixture was then allowed to warm to 0° and treated with excess sodium bicarbonate solution. The organic phase was separated and the organic phase extracted twice with chloroform. The combined organic phases were washed with brine, dried over magnesium sulphate and evaporated. The product was obtained by column chromatography of the residue (Kieselgel, ethyl acetate as eluent), and recrystallisation from ethyl acetate/cyclohexane.

Yield = 125 mg. m.pt. 94°–96°.

$[\alpha]_D^{20}$ +39.9.

I.R. $v_{max}$ (Nujol) 3350, 3170, 1790, 1740, 1672 and 1640 cm$^{-1}$.

N.M.R. δ(CDCl$_3$) 3.05 (1H, d, J=17 Hz), 3.51 (1H, dd, J=3 and 17 Hz), 3.78 (3H, s), 3.88 (2H, s), 4.15 (2H, d, J=7 Hz), 4.84 (1H, broad t, J=7 Hz), 5.08 (1H, broad s), 5.70 (1H, d, J=3 Hz), 6.0–6.7 (2H, broad).

EXAMPLE 6 tert-Butylammonium 9-O-carboxamidomethylclavulanate

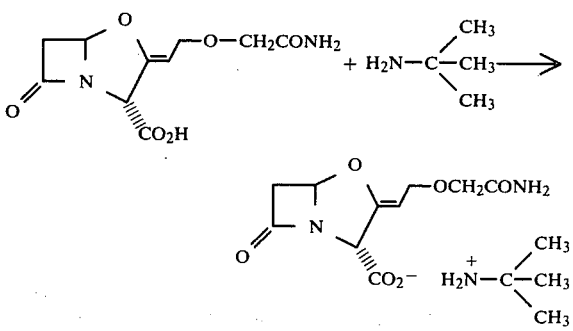

9-O-Carboxamidomethyl clavulanic acid (83 mg) was stirred with tetrahydrofuran (20 ml) for 10 mins and the solution filtered. A solution of tert-butylamine (23.6 mg) in ether (1 ml) was then added and the solution was evaporated to about ⅓ its volume. Ether was slowly added to precipitate the product. The white crystalline material was filtered off, washed with ether and dried under vacuum.

Yield 78 mg.

I.R. $v_{max}$ (KBr) 1805, 1680, 1580 cm$^{-1}$.

N.M.R. δ (D₂O) 1.34 (9H, s), 3.06 (1H, d, J=17 Hz), 3.54 (1H, dd, J=3 and 17 Hz), 3.96 (2H, s), 4.16 (2H, d, J=7 Hz), 4.88 (1H, broad t, J=7 Hz), 4.92 (1H, broad s), 5.69 (1H, d, J=3 Hz).

Analysis found: C, 50.75; H, 6.85; N, 12.53.
C₁₄H₂₃N₃O₆ requires: C, 51.05; H, 7.04; N, 12.76.

EXAMPLE 7

9-O-Carboxamidomethyl clavulanic acid

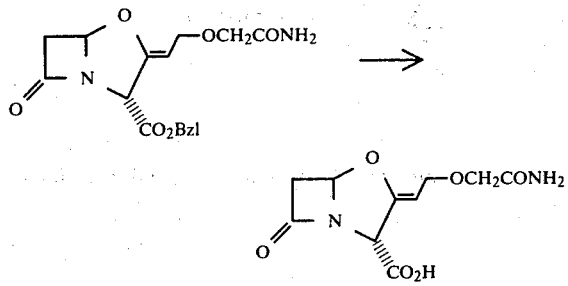

A solution of benzyl 9-O-carboxamidomethyl clavulanate (1.309 gm) in tetrahydrofuran (35 ml) was hydrogenated over 10% palladium charcoal (400 mg) for 20 mins. The solution was filtered through celite and the filter cake washed well with tetrahydrofuran. The solution was then concentrated and cooled to 0°. The crystallised product was filtered off and dried under vacuum.

Yield 561 mg. m.pt. 120–126 dec.

I.R. $\nu_{max}$ (Nujol) 3440, 3320, 1793, 1715, 1695 and 1635 cm⁻¹.

EXAMPLE 8

Composition a. Sodium 9-O-carboxamidomethylclavulanate (100 mg) may be dissolved in water for injection BP (1 ml) to form an injectable solution.

b. Sodium 9-O-carboxamidomethylclavulanate (100 mg) may be dissolved in water for injection BP (1 ml) and mixed with a solution of sodium amoxycillin (250 mg) in water for injection BP (1 ml) and the solutions mixed to form an injectable solution.

DEMONSTRATION OF BIOLOGICAL EFFECTS

The synergist referred to hereinafter is sodium 9-O-carboxamidomethylclavulanate.

The synergist demonstrated synergy in standard MIC tests as follows:

| | MIC (μg/ml) of Ampicillin | | | |
|---|---|---|---|---|
| μg/ml synergist | Staph. Russell | Kleb. E 70 | Proteus C889 | E. Coli JT 39 |
| 20 | ≦0.2 | 0.2 | 1 | ≦0.5 |
| 5 | 0.16 | 3.1 | 2 | 2 |
| 1 | 0.62 | 1.6 | 4 | 2 |
| 0 | >32 | >32 | >32 | >32 |
| Synergist alone* | 31 | 31 | | 31 |

*MIC (μg/ml) obtained in separate test

When administered at a dose of 2 mg/kg subcutaneously to mice suffering from an E. coli JT 39 infection the compound of this example reduced the CD₅₀ of amoxycillin to about 12 mg/kg×2 (c.f.-CD₅₀ of amoxycillin when 2 mg/kg of sodium clavulanate employed is about 18 mg/kg×2 CD₅₀ of amoxycillin alone is greater than 500 mg/kg×2 and at 2 mg/kg×2 the compound of this example has no effect).

The synergist did not cause animal deaths due to toxic effects during testing at therapeutic doses. No overt toxic symptoms were observed.

I claim:

1. The compound of the formula (I):

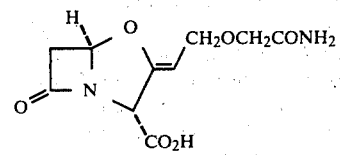

a pharmaceutically acceptable salt thereof or an ester thereof of the formula (II) or (III):

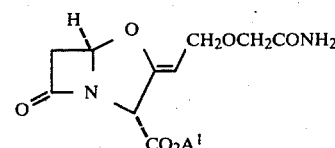

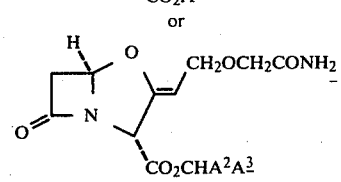

wherein A¹ is alkyl of up to 4 carbon atoms, alkenyl of up to 4 carbon atoms, alkynyl of up to 4 carbon atoms or alkyl of up to 4 carbon atoms mono-substituted by halogen, hydroxyl, alkoxyl or alkanoyloxy of up to 4 carbon atoms, acetyl or benzoyl; A² is hydrogen, phenyl, chlorophenyl, methoxyphenyl, bromophenyl or nitrophenyl; and A³ is phenyl, chlorophenyl, methoxyphenyl, bromophenyl or nitrophenyl.

2. A pharmaceutically acceptable salt of the compound of claim 1.

3. A compound according to claim 1 in the form of an ester of the formula (II) or (III):

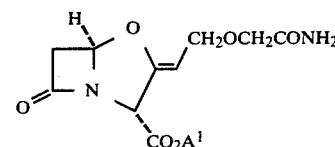

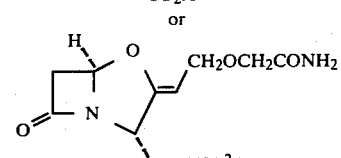

wherein A¹ is alkyl of up to 4 carbon atoms, alkenyl of up to 4 carbon atoms, alkynyl of up to 4 carbon atoms or alkyl of up to 4 carbon atoms mono-substituted by halogen, hydroxyl, alkanoyloxy or acyloxyl of up to 4 carbon atoms, acetyl or benzoyl; A² is hydrogen, phenyl, chlorophenyl, methoxyphenyl, bromophenyl or nitrophenyl; and A³ is phenyl, chlorophenyl, methoxyphenyl, bromophenyl or nitrophenyl.

4. An ester of the formula (IV):

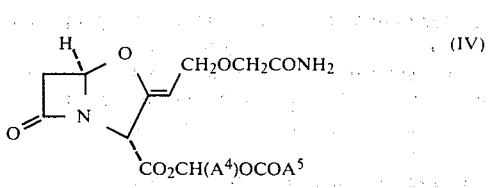 (IV)

wherein $A^4$ is hydrogen or methyl, $A^5$ is alkyl or alkoxyl of up to 4 carbon atoms or a phenyl or benzyl group or $A^4$ is attached to $A^5$ to form a phenyl ring.

5. The compound according to claim 1 which is benzyl 9-O-carboxamidomethylclavulanate.

6. The compound according to claim 1 which is sodium 9-O-carboxamidomethylclavulanate.

7. The compound according to claim 1 which is p-nitrobenzyl 9-O-carboxamidomethylclavulanate.

8. The compound according to claim 1 which is methoxymethyl 9-O-carboxamidomethylclavulanate.

9. The compound according to claim 1 which is tert-butylammonium 9-O-carboxamidomethylclavulanate.

10. An alkaline earth metal salt of a compound of claim 1.

11. The lithium, sodium, potassium, calcium, magnesium, ammonium or alkylamine salt of a compound of claim 1.

12. A soluble non-pharmaceutically acceptable salt of a compound of the formula (I):

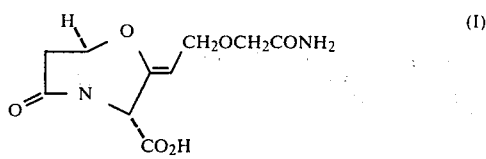 (I)

13. An alkaline metal salt of a compound of claim 1.

* * * * *